(12) United States Patent
Ohman et al.

(10) Patent No.: US 8,759,115 B2
(45) Date of Patent: Jun. 24, 2014

(54) ASSAY DEVICE

(71) Applicant: ÅMIC AB, Uppsala (SE)

(72) Inventors: Per Ove Ohman, Uppsala (SE); Ib Mendel-Hartvig, Uppsala (SE); Tomas Lindstrom, Uppsala (SE)

(73) Assignee: Johnson & Johnson AB, New Brunswick, NJ (US)

( * ) Notice: Subject to any disclaimer, the term of this patent is extended or adjusted under 35 U.S.C. 154(b) by 0 days.

(21) Appl. No.: 13/712,230

(22) Filed: Dec. 12, 2012

(65) Prior Publication Data

US 2013/0203183 A1    Aug. 8, 2013

Related U.S. Application Data

(62) Division of application No. 12/305,641, filed as application No. PCT/SE2007/050445 on Jun. 20, 2007, now Pat. No. 8,343,439.

(30) Foreign Application Priority Data

Jun. 20, 2006  (SE) ........................... 0601353

(51) Int. Cl.
   *B01L 3/00*       (2006.01)
   *G01N 33/543*   (2006.01)
   *G01N 33/558*   (2006.01)

(52) U.S. Cl.
   CPC ......... *G01N 33/543* (2013.01); *B01L 2300/087* (2013.01); *B01L 2300/0825* (2013.01); *B01L 2300/089* (2013.01); *B01L 2400/086* (2013.01); *B01L 2300/025* (2013.01); *B01L 2200/025* (2013.01); *B01L 3/502746* (2013.01); *B01L 2400/0406* (2013.01); *G01N 33/558* (2013.01); *Y10S 436/807* (2013.01)

USPC ............ 436/517; 436/536; 436/56; 436/164; 436/807

(58) Field of Classification Search
   USPC .............................. 436/807, 517, 536, 56, 164
   See application file for complete search history.

(56) References Cited

U.S. PATENT DOCUMENTS 5,356,785 A    10/1994   McMahon et al.
6,143,576 A    11/2000   Buechler
(Continued)

FOREIGN PATENT DOCUMENTS

EP         1271150 A2     1/2003
JP         2005-532151    10/2005
(Continued)

OTHER PUBLICATIONS

European Search Report mailed Sep. 14, 2009, for EP Application No. 07748605.8 filed Jan. 19, 2009, 4 pages.

(Continued)

*Primary Examiner* — Jill Warden
(74) *Attorney, Agent, or Firm* — Hiscock & Barclay, LLP

(57) ABSTRACT

An assay device for performing an assay on a liquid sample using a detection conjugate capable of binding to an antigen and containing a label. The device includes a substrate surface having a sample addition zone, a reaction zone and an absorbing zone, the zones being connected by at least one fluid passage, wherein the device has a first functionality verifying feature located between the sample addition zone and the reaction zone, and a second functionality verifying feature located within the absorbing zone. Both functionality verifying features are capable of undergoing a detectable change when contacted by the sample, in which the assay device further includes at least one alignment verification zone. There is further provided a kit of parts and a method of conducting an assay.

8 Claims, 2 Drawing Sheets

(56) References Cited

U.S. PATENT DOCUMENTS

| | | | |
|---|---|---|---|
| 6,156,270 | A | 12/2000 | Buechler |
| 6,565,808 | B2 | 5/2003 | Hudak et al. |
| 6,767,510 | B1 | 7/2004 | Buechler |
| 6,906,802 | B2 | 6/2005 | Voelkel |
| 6,916,666 | B1 | 7/2005 | Mendel-Hartvig et al. |
| 7,267,799 | B1 | 9/2007 | Borich et al. |
| 8,025,854 | B2 | 9/2011 | Ohman et al. |
| 8,343,439 | B2 * | 1/2013 | Ohman et al. ............... 422/502 |
| 2003/0035758 | A1 | 2/2003 | Buechler et al. |
| 2004/0077103 | A1 | 4/2004 | Buechler |
| 2004/0126767 | A1 | 7/2004 | Anderberg et al. |
| 2005/0042766 | A1 | 2/2005 | Ohman et al. |
| 2005/0136552 | A1 | 6/2005 | Buechler |
| 2006/0078986 | A1 | 4/2006 | Ly et al. |

FOREIGN PATENT DOCUMENTS

| | | |
|---|---|---|
| WO | WO 98/22824 A1 | 5/1998 |
| WO | WO 00/77524 A1 | 12/2000 |
| WO | WO 03/023371 A1 | 3/2003 |
| WO | WO 03/103835 A1 | 12/2003 |
| WO | WO 03/103835 A1 | 12/2003 |
| WO | WO 2004/003559 A1 | 1/2004 |
| WO | WO 2005/059082 A3 | 9/2005 |
| WO | WO 2005/089082 A2 | 9/2005 |
| WO | WO 2005/116632 A2 | 12/2005 |
| WO | WO 2005/118139 A1 | 12/2005 |
| WO | WO 2005/118139 A2 | 12/2005 |
| WO | WO 2006/039542 A1 | 4/2006 |
| WO | WO 2006/105110 A2 | 10/2006 |

OTHER PUBLICATIONS

Japanese Office Action for JP Application No. 2009-516453; dated Jan. 31, 2012; 3 pages.

International Preliminary Report on Patentability completed Aug. 28, 2008, for PCT Application No. PCT/SE2007/050445 filed Jun. 20, 2007; 7 pages.

International Preliminary Report on Patentability mailed Oct. 24, 2007, for PCT Application No. PCT/SE2007/050445 filed Jun. 20, 2007; 4 pages.

International Preliminary Report on Patentability mailed Jun. 12, 2008, for PCT Application No. PCT/SE2007/050445 filed Jun. 20, 2007; 7 pages.

International Preliminary Report on Patentability mailed Oct. 24, 2007, for PCT Application No. PCT/SE2007/050445 filed Jun. 20, 2007; 7 pages.

Canadian Office Action for CA Application No. 2,654,931; dated Jan. 30, 2013; 4 pages.

* cited by examiner

ASSAY DEVICE

CROSS REFERENCE TO RELATED APPLICATIONS

This application is a divisional application of U.S. Ser. No. 12/305,641, filed on May 27, 2009, which claims priority to PCT/SE/2007/050445, filed Jun. 20, 2007 and Swedish patent application Serial No. 0601353-6, filed Jun. 20, 2006, the entire contents of which are each being incorporated herein by reference.

TECHNICAL FIELD

The present invention concerns assay devices and means for improving their reliability. The invention concerns in particular a method and device, wherein features integrated in the assay device are used for verifying the correct function of the assay device and optional auxiliary devices, such as a reader.

BACKGROUND

Many biochemical tests which previously were performed in the laboratory using advanced equipment and skilled technicians, can today be performed by a physician, a nurse or even the patient himself/herself, using small and often disposable devices. This is a result of a better understanding of biochemistry and medicine, as well as miniaturization of both mechanics and electronics.

Such tests can be divided into two groups: "one-step tests" where a reaction takes place on a substrate after the addition of sample, and the result is detected as a change of one or more properties of said substrate; and "two-step tests", where the sample is followed by the addition of a detection conjugate, leading to a specific reaction resulting in a detectable signal.

In many assay devices, the detection conjugate and possible other reagents are pre-dispensed or integrated in the device, setting aside the need for separate addition of reagents by the user.

The most common type of disposable assay device consists of a zone or area for receiving the sample, a reaction zone, and optionally a transport or incubation zone connecting the receiving and reaction zone, respectively. These assay devices are known as immunochromatography assay devices or simply referred to as strip tests. They employ a porous material, such as nitrocellulose, defining a fluid passage capable of supporting capillary flow. The sample-receiving zone frequently consists of a more porous material, capable of absorbing the sample, and, when the separation of blood cells is desired, effective to trap the red blood cells. Examples of such materials are fibrous materials, such as paper, fleece, gel or tissue, comprised e.g. of cellulose, nitrocellulose, wool, glass fibre, asbestos, synthetic fibers, polymers, etc. or mixtures of the same. The transport or incubation zone commonly consists of the same or similar materials, often with different porosity than that of the sample-receiving zone. Likewise, the reaction zone, which may be integrated with the incubation zone, or constituting the most distal part thereof, commonly consists of similar, absorbing fibrous materials, such as nitrocellulose, or any of the above listed materials.

In an assay device or strip test, the porous material(s) are assembled on a carrier, such as a strip of thermoplastic material, paper, cardboard or the like. In one embodiment, a cover is provided, said cover having at least one aperture for receiving the sample, and an aperture or a transparent area for reading the result of the assay.

It is most often desirable to minimize the sample volume, in line with the tendency to miniaturize the entire test, including minimizing the amounts of reagents, without compromising accuracy and reliability.

Many assays are used in a clinical setting, for the rapid determination of various analytes, indicative of particular diseases. Many assays find utility in the physician's office, making it possible to convey the result to the patient during one and the same visit. Other assays are used in a point of care or even an emergency room setting, where a rapid and reliable result is of great importance, decisive for the choice of treatment.

While handy to use and often relatively rapid, there is still room for an improvement regarding the means for indicating the proper functioning of the assay devices. Rapid in this context means that the result can be read within about a few minutes or shorter to about 20 minutes or longer from the application of the sample to the assay device.

Another feature that would be valuable from a user perspective is be an internal calibration. One example of prior approaches to this question is shown in U.S. Pat. No. 5,356,785, describing an immunoassay having a reference area providing a detectable signal, in addition to a first and second test area, each of which contains a different amount of a first and second member of the specific binding pair. Thus the intensity of the detectable signal from the reference area is in one embodiment compared with the intensity of any detectable signal from the two test areas in the presence of an unknown quantity of the first binding pair member in the sample. This way it is no longer necessary to run standards and compare the test result to such standards.

An assay device is often used together with a reader, which reads or senses a signal from the assay device. Often the assay devices are disposable while the reader is used multiple times. It is necessary to have an interaction between the assay device and the reader. One problem in connection with an assay device and a reader is how to correctly align of the assay device in relation to the reader to give the desired reading. Another problem is how to verify the correct alignment of the assay device relative to the reader.

Problems in the state of the art regarding assay devices to be used together with a reader include how to align the assay device in a reader, how to calibrate the device, how to check the flow in the assay device, how to check whether the reactants have dissolved properly, how to check that the assay is ready, how to verify correct function of the assay, and how to improve the speed of the checks and verifications.

From WO2005118139 there is known a device for handling liquid samples, comprising an area having projections substantially vertical to its surface, whereby the projections create a capillary force. In such assay devices there arises new problems compared to earlier assay devices without projections creating a capillary force. For a reliable assay it is necessary to verify the correct function of the assay including the alignment of the assay device in the reader.

In the light of the background art, known to the inventors, there appears to be a need of an improved method and device, verifying the proper functioning of an assay and/or giving the user a rapid indication in case the assay or the optional reader does not function properly.

Other problems and the solutions associated therewith will become evident to the skilled person upon study of the description, examples, claims and drawings.

SUMMARY OF THE INVENTION

It is an object of the present invention to alleviate at least some of the problems in the background art.

The present inventors have made available an improved assay device with integrated functionality verification features, as defined in the claims.

Embodiments of the inventive device and method are described in the following description, examples, drawings and claims, hereby incorporated by reference.

SHORT DESCRIPTION OF THE DRAWINGS

The invention will be described in detail in the following description, non-limiting examples, and claims, with reference to the attached drawings, in which FIG. 1 shows schematically one embodiment of an assay device or a part thereof;

DESCRIPTION OF THE INVENTION

Figure 1:
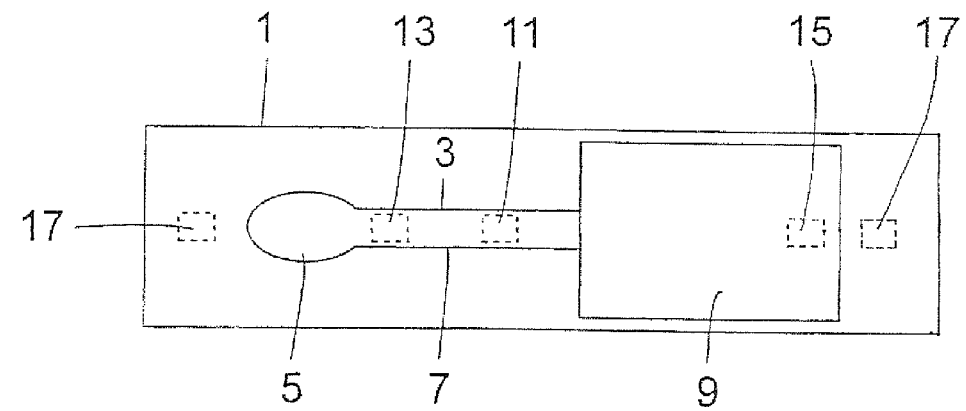

Before the present device and method is described, it is to be understood that this invention is not limited to the particular configurations, method steps, and materials disclosed herein as such configurations, steps and materials may vary somewhat. It is also to be understood that the terminology employed herein is used for the purpose of describing particular embodiments only and is not intended to be limiting since the scope of the present invention will be limited only by the appended claims and equivalents thereof.

It must also be noted that, as used in this specification and the appended claims, the singular forms "a", "an", and "the" include plural referents unless the context clearly dictates otherwise. Thus, for example, reference to a reaction mixture containing "a monoclonal antibody" includes a mixture of two or more antibodies.

The term "about" when used in the context of numeric values denotes an interval of accuracy, familiar and acceptable to a person skilled in the art. Said interval is ±10% or preferably it is ±5%.

In describing and claiming the present invention, the following terminology will be used in accordance with the definitions set out herein.

The term "sample" here means a volume of a liquid, solution or suspension, intended to be subjected to qualitative or quantitative determination of any of its properties, such as the presence or absence of a component, the concentration of a component, etc. Examples of subjects from which the sample is taken include an organism, such as a mammal, and a human; or from the biosphere, such as a water sample, or an effluent; or from an technical, chemical or biological process, such as a process of manufacturing, e.g. the production of medicaments, food, feed, or the purification of drinking water or the treatment of waste effluents. The sample may be subjected to qualitative or quantitative determination as such, or after suitable pre-treatment. Non-limiting examples of pre-treatment include homogenization, sonication, filtering, sedimentation, centrifugation, and heat-treatment.

Examples of samples in the context of the present invention include body fluids such as blood, plasma, serum, lymph, urine, saliva, semen, amniotic fluid, gastric fluid, phlegm, sputum, mucus, and tears; environmental fluids such as surface water, ground water, and sludge; and process fluids such as milk, whey, broth, nutrient solutions, and cell culture medium. Embodiments of the present invention are applicable to all samples. In one embodiment the present invention is applicable to samples of body fluids. In another embodiment, the present invention is applicable to whole blood samples.

The determination based on lateral flow of a sample and the interaction of components present in the sample with reagents present in the device and detection of such interaction, either qualitatively or quantitatively, may be for any purpose, such as diagnostic, environmental, quality control, regulatory, forensic or research purposes. Such tests are often referred to as chromatography assays, or lateral flow assays, as in e.g., immunochromatography assays.

Examples of diagnostic determinations include, but are not limited to, the determination of analytes, also called markers, specific for different disorders, e.g. chronic metabolic disorders, such as blood glucose, blood ketones, urine glucose (diabetes), blood cholesterol (atherosclerosis, obesitas, etc); markers of other specific diseases, e.g. acute diseases, such as coronary infarct markers (e.g. troponin-T), markers of thyroid function (e.g. determination of thyroid stimulating hormone (TSH)), markers of viral infections (the use of lateral flow immunoassays for the detection of specific viral antibodies); etc.

Another important field of diagnostic determinations relate to pregnancy and fertility, e.g. pregnancy tests (determination of i.a. human chorionic gonadotropin (hCG)), ovulation tests (determination of i.a. luteneizing hormone (LH)), fertility tests (determination of i.a. follicle-stimulating hormone (FSH)), etc.

Yet another important field is that of drug tests, for easy and rapid detection of drugs and drug metabolites indicating drug abuse; such as the determination of specific drugs and drug metabolites (e.g. THC) in urine samples, etc.

The term "analyte" is used as a synonym of the term "marker" and intended to encompass any substance that is measured quantitatively or qualitatively.

The terms "zone", "area" and "site" are used in the context of this description, examples and claims to define parts on a substrate, either in prior art devices or in a device according to an embodiment of the present invention.

The term "reaction" is used to define any reaction, which takes place between components of a sample and at least one reagent or reagents on or in said substrate, or between two or more components present in said sample. The term "reaction" is in particular used to define the reaction, taking place between an analyte and a reagent as part of the qualitative or quantitative determination of said analyte.

The term "substrate" here means the carrier or matrix to which a sample is added, and on or in which the determination is performed, or where the reaction between analyte and reagent takes place.

The term "chemical functionality" comprises any chemical compound or moiety necessary for conducting or facilitating the assay. One group of chemical compounds, with particular relevance in the present invention, are compounds or components exhibiting specific affinity to, or capability of binding or interacting with, one or more components in the sample. Red blood cell separating agents constitute an illustrative example. Such agents may be any substance capable of aggregating or binding red blood cells.

The term "biological functionality" comprises all biological interactions between a component in a sample and a reagent on or in the substrate, such as catalysis, binding, internalization, activation, or other bio-specific interaction. Suitable reagents include, but are not limited to, antibodies, antibody fragments and derivates, single chain antibodies, lectines, DNA, aptamers, etc., including other polymers or molecules with binding capacity. Such reagents can be identified by a person skilled in the art, following the choice of the component to be separated, using standard experimentation, e.g., screening methods and chemical libraries.

The term "physical functionality" here comprises functionalities involved in reactions and interactions other than those that are mainly chemical or biological. Examples include diameter, height, shape, cross section, surface topography and surface patterns, the number of projections per unit area, wetting behavior of the surface of said projections, or a combination thereof, and/or other functionalities influencing the flow, retention, adhesion or rejection of components of the sample.

The distinctions between chemical, biological and physical interactions are not always clear, and it is possible that an interaction—such as an interaction between a component in a sample and a reagent on the substrate—involves chemical, biological as well as physical zones.

The terms "hydrophilic" and "hydrophobic", as in hydrophilic or hydrophobic compounds, hydrophilic or hydrophobic interactions etc., have the meaning generally understood by a person skilled in the art, and corresponding to that used in generally recognized textbooks.

Assays are classified according to many factors, such as their use, the operating principle etc. The two major groups and also the factor that has greatest influence on the performance that can be expected of an assay with regard to precision and sensitivity are the competitive assays, i.e., the assays using a limited amount of antibody; and
the solid phase sandwich assays, characterized by the use of an excess amount of antibody, also called immunometric assays.

In the competitive assay format, the amount of antibody is insufficient to hind all of the antigens. A fixed amount of labelled antigen competes with the unlabelled antigen from the sample for the limited amount of antibody binding sites. The concentration of antigen in the sample can be determined from the proportion of labelled antigen that is bound to the antibody or alternatively that is free.

In the sandwich assay format, an antigen in the sample binds to excess of antibodies on the solid phase. The bound antigen is then detected with a second labelled antibody. In this instance, the amount of labelled antibody captured on the solid phase is directly proportional to the amount of antigen in the sample.

In both these basic designs of immunoassays and the various variants thereof there is a considerable need for standardization and control of the assay and the environment the assay is run in. The present invention solves some of the problems connected with solid phase lateral flow immunoassay. One of the crucial steps is the solubilisation and transport of the detection conjugate. Another important step is the separation of red blood cells where there is a high risk for cell lysis and blood clotting. Furthermore, in many instances there is a need for rapid information regarding the progression of the assay as in for example an emergency room setting. Measuring the progression of the liquid/conjugate front, as disclosed by the inventors solves the above problems. Furthermore, continuous measuring the moving conjugate also gives information of the exact amount of conjugate that will be involved in the immune detection. This information together with the kinetics of the conjugate release could also be used in calculating and/or correction of the assay result.

Another problem is the alignment of the assay device in a reader and verification of the alignment in a reader. This is solved by having at least one alignment verification zone on the assay device.

The invention is not restricted to the assay format described above but could of course also be adapted to other assay format well known for persons skilled in the art.

The inventors realized that many factors must be taken into account in order to address the needs of the users. First, the user must get a confirmation of the correct initiation of the assay, that the sample has been correctly applied, that the assay device functions as it should, and that the assay device is correctly aligned. In the absence of a verification of correct function, the user needs to be alerted immediately, so that another assay device can be used. Waiting for the completion of a faulty test would simply lead to the loss of valuable time, in particular in an emergency room setting. Second, the user needs a confirmation that the assay has functioned properly and the reactions come to an end, for example that the desired sample volume has been subjected to the assay. In the absence of such confirmation, the result cannot be completely trusted.

These issues were surprisingly addressed by defining at least two areas on the assay device, one first area in the fluid passage downstream from the sample addition zone and close to this zone, and one second area in absorbing zone and by having at least one alignment verification zone on said assay device.

According to the present invention there is in a first aspect provided an assay device for performing an assay on a liquid sample using a detection conjugate capable of binding to an antigen and containing a label, the device comprising a substrate having a substrate surface, wherein the surface comprises projections substantially perpendicular to the surface, the projections having a height, diameter and distance capable of generating lateral capillary flow of a fluid in the passage, the surface comprising a sample addition zone, a reaction zone and an absorbing zone, the zones being connected by at least one fluid passage, wherein the device has a first functionality verifying feature located between the sample addition zone and the reaction zone, and a second functionality verifying feature located within the absorbing zone, and both functionality verifying features being features capable of undergoing a detectable change when contacted by the sample, the assay device further comprising at least one alignment verification zone.

In one embodiment the functionality verifying features, the reaction zone and the alignment verification zone are aligned in a straight line.

In one embodiment there are two alignment verification zones. This has the advantage of a better and more accurate alignment in the reader.

In one embodiment the assay device comprises a third zone containing the same label as used in the detection conjugate in a known and well defined amount. This is used as a zone for calibration. In an alternative embodiment there are several zones for calibration.

In one embodiment the detectable change is a colour change triggered by the sample wetting the first and second functionality verifying feature in the fluid passage and the absorbing zone, respectively.

In one embodiment the detectable change is a measurable fluorescence, detected as surplus detection conjugate reaches the fluid passage and the absorbing zone, respectively.

In one embodiment the substrate is transparent to the detectable change. In one embodiment the third zone used for calibration is an area of projections exhibiting the same height, diameter and distance as the projections in the fluid passage, but which zone is not in fluid connection therewith.

In a second aspect of the present invention there is provided a kit of parts comprising an assay device according to the invention and a reader, the reader comprising at least one reading means capable of reading a detectable signal from the assay device, the device further comprising at least one alignment function. The reader is intended to be used to read the result of the assay. In one embodiment the sample is applied to the assay device and then the assay device is inserted into the reader. In one embodiment the assay device is automatically aligned in the reader by an alignment function in the reader. The reader reads the detectable signals from the assay device and thereby verifies the correct function of the assay and correct alignment of the device in the reader. If the proper function is not verified a signal to the used is given in one embodiment.

There is further provided a reader comprising one reading means aligned in a straight line. This has the advantage that only one detector needs to be used in the reader to verify the correct function and the correct alignment of the assay device in the detector. In one embodiment either the detector or the assay device is moved along the straight line along which the reaction zone, the functionality verifying features, the calibration zone and the alignment verification zones are aligned.

In a third aspect of the present invention there is provided a method of conducting an assay comprising verification of the alignment of an assay device in a reader using at least one alignment verification zone, the addition of a sample and the detection of at least one reaction between the sample and one or more reagents using a device having at least one fluid passage, a sample addition zone and an absorbing zone, wherein a first reaction between the sample and one or more reagents is detected in the fluid passage, in a first area downstream from the sample addition zone, and the absence of signal or an insufficient signal is taken as an indication of error.

In one embodiment an error message is displayed without delay, and the user prompted to remove the assay device and attempt a new assay.

In one embodiment the method includes a calibration step, wherein the amount of at least one label, pre-dispensed in a third area of the assay device, separate from the fluid passage, is determined and the value compared to a preset value.

In one embodiment the result of the analysis is adjusted based on the result of the calibration.

In one embodiment a margin or error, based on the result of the calibration, is displayed to the user together with the result of the analysis.

In one embodiment the label on the third zone is the same label as used in the detection conjugate.

The presence of sample or a mixture of sample and detection conjugate in the first area confirms that the sample has been properly added, that possible pretreatment steps such as the removal of red blood cells, have functioned, and that the lateral capillary flow has started.

In the second area, the presence of surplus label is evidence that sample has been drawn through the entire length of the fluid passage. In an assay device where sample volume is determined by the capacity of the absorbing zone and the fluid passage, the detection of label in the distal part of the absorbing zone indicates that the absorbing zone is full, and that the correct sample volume has passed the reaction zone.

Thirdly, and optionally, the user has benefit from a calibration being performed in conjunction with each assay. The calibration is conducted using the third zone. Normally, readers used in the context of assay devices have a stand-by mode and possible self-test programs. In addition to that, the reader needs to be tested and calibrated at regular intervals. It is easily understood that this can be a problem for apparatuses used in an emergency room setting, or in ambulatory medical settings. Problems may also arise in cases where an apparatus is infrequently used, or handled by unskilled personnel or by the patient himself/herself.

For increasing reliability and simplifying the use of assays, where the result is determined with the aid of an apparatus reading the presence of a signal, e.g. the concentration of a label or marker substance at a particular location on the assay device, the present inventors developed means and a method for confirming proper function and an instant and internal calibration.

According to one embodiment of the invention, the same label or marker substance as used in the assay, is deposited in an area on the assay device, separate from the fluid passage. This makes it possible to use a known and accurately determined amount of the label. This amount of label can be used as an internal standard, making it possible to calibrate the reader at the onset of each determination. In case the reader detects a signal within a pre-determined margin of error, it is assumed that the reader is operational and it is calibrated. If the reader detects a signal outside said margin of error, it is assumed that the reader is non-operational and needs maintenance.

Separated from the fluid passage, an third zone is defined in one embodiment. According to one embodiment, the third zone consist of the same substantially vertical projections as in the fluid passage and the absorbing zone. In other, alternative embodiments, the third zone is defined as a well, a dent or depression in the substrate surface, or any other feature defining an area on the substrate surface. In at least one of the third zones, a known and well-defined amount of a label is deposited. In one embodiment the functionality verification zones and the alignment verification zone are aligned with the reaction zone and the entire fluid passage.

In one embodiment the alignment verification zone(s) are also zones for calibration, where at least one of the alignment verification zones comprise the same label as used in the detection conjugate in a known and defined amount.

FIG. 1 shows one embodiment of the present invention with two zones for verification of the alignment in the reader, wherein at least one of the two alignment verification zones comprise the same label as used in the detection conjugate in a known and defined amount. The embodiment illustrated in FIG. 1, shows a substrate 1, an area of substantially vertical projections define a fluid passage 3, comprising a sample addition zone 5, a reaction zone 7 and an absorbing zone 9. The determination of the assay result includes a reading of a signal, e.g., a label coupled to a detection conjugate, in the area 11. In the fluid passage, downstream from the sample addition zone, a first area 13 is defined. Similarly, in the most proximal part of the absorbing zone, a second area 15 is defined. Separated from the fluid passage, two alignment verification zones 17 are defined. According to one embodiment, the alignment verification zones 17 consist of the same substantially vertical projections as in the fluid passage and the absorbing zone. In other, alternative embodiments, the areas 17 are defined as a cross, a circle, an elevation, a well, a dent or a depression in the substrate surface, or any other feature defining a spot on the substrate surface. Note that these functionality verification features areas 13, 15, are, in this embodiment, aligned with the alignment verification zone as well as the reaction zone 11 and the entire fluid passage.

Figure 2:
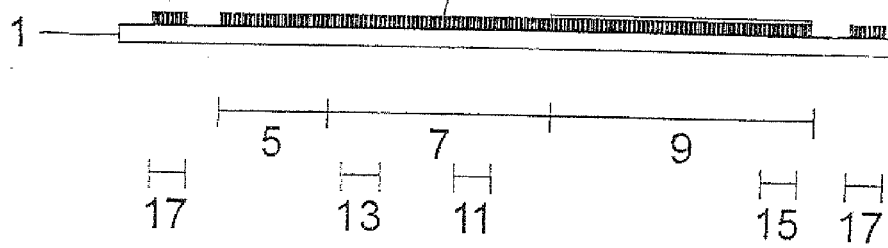
FIG. 2 shows a side view of the above embodiment.

FIG. 2 shows schematically the same embodiment from the side, indicating the relative position of the different features, but not their size or proportions, as the figure is not to scale. It is shown that a cover or foil 9 is positioned on the absorbing zone, in order to define the volume thereof with increased accuracy. Except the cover 9 the system is open, i.e. there is no lid in capillary contact with the projections.

Figure 3:
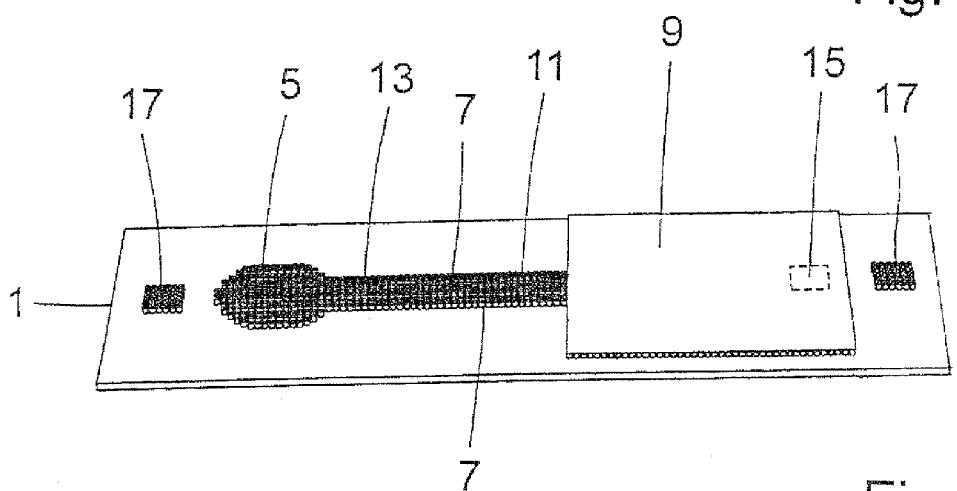
FIG. 3 is a perspective view of the same embodiment.

FIG. 3 shows a perspective view of the same embodiment. Here the sample addition zone is shown as consisting of perpendicular projections, but it can also be a basin or reservoir, bordering to the reaction zone. Such basin or reservoir can be a depression in the surface of the substrate, and it may contain the substantially perpendicular projections described above, on all or part of its surface. It is conceived that the projections have another shape, or dimensions than the projections constitution the fluid passage leading to the absorption zone.

Figure 4:
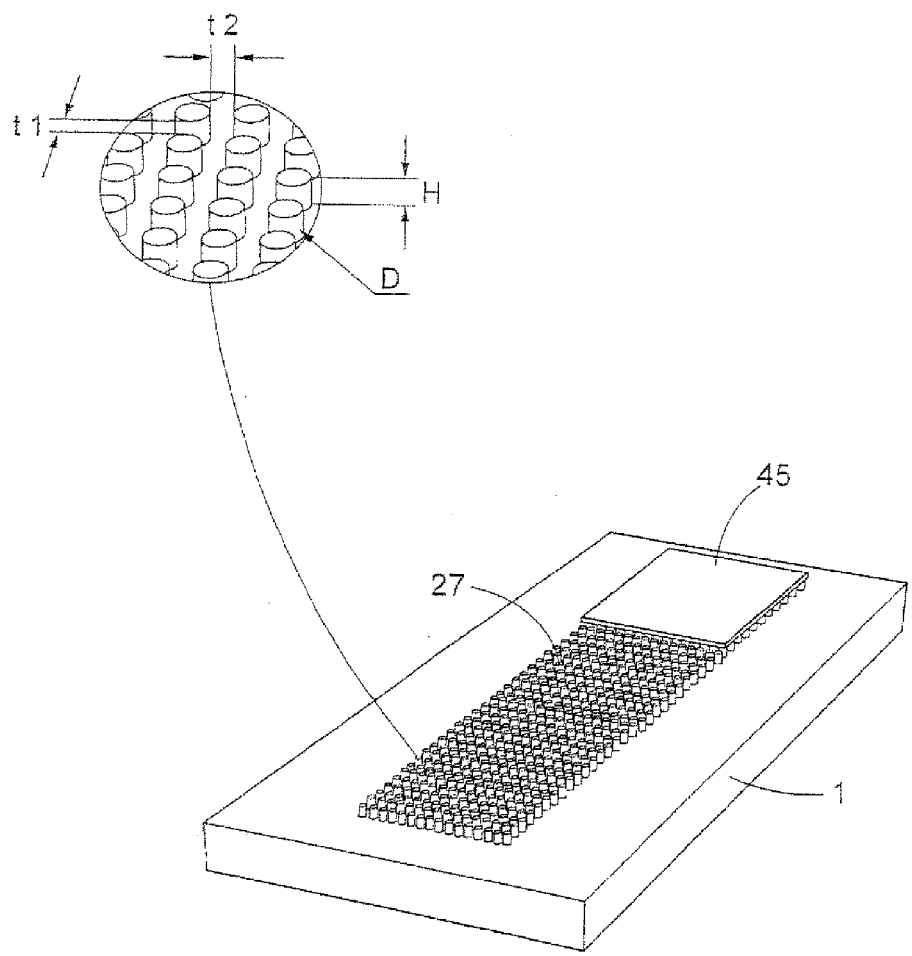
FIG. 4 is a perspective view of another embodiment.

FIG. 4 shows an embodiment where on a substrate 1, a fluid passage 27 is achieved by arranging an area of projections substantially perpendicular to the substrate surface, said projections having a height (H), diameter (D) and a distance or distances between the projections (t1, t2) such, that lateral capillary flow of said fluid in said zone is achieved. The detail view in FIG. 4 shows how these measures are taken. Also in this embodiment, a foil 45 is arranged on the projections, creating an absorbing zone with a well defined volume.

In an assay device of the invention, the substantially perpendicular projections are in one embodiment given a chemical, biological or physical functionality suitable for the particular assay where they are employed. The projections in the fluid passage and the absorbing zone are in one embodiment given hydrophilic properties, suitable for the desired flow capacity and flow rate. One way of adjusting the hydrophilic properties is the deposition of dextran on the projections.

The inventors also make available a method of verifying the functionality of the assay device for assaying a fluid sample. In the method, the presence of a label is first determined in a first area downstream from the sample addition zone, and the absence of label or an insufficient amount of label is taken as an indication of error. The method comprises verification of proper alignment of the assay device in the reader. In one embodiment an error message is displayed without delay, and the user prompted to remove the assay device and attempt a new assay. The presence of sample, or a mixture of sample and detection conjugate, is taken as a sign that sample has been properly added and that an initial dissolution and transport of the mixture of sample and detection conjugate has begun.

According to the invention, the presence of the mixture of sample and detection conjugate is then determined in an second area in the distal part of the absorbing zone, wherein the absence of label or insufficient amounts thereof is taken as an indication of an error. In one embodiment an error message is displayed without delay, and the user prompted to remove the assay device and attempt a new assay. The presence of label in the second area is taken as a sign that the test strip functions and that the desired amount of sample has passed the reaction zone.

In one embodiment the detector of the reader is used to verify the correct alignment of the assay device in the reader. If the assay device is misaligned in the reader this will be detected because of the position of the at least one alignment verification zone on the assay device. In case of a misalignment, the reader will in one embodiment alert the user. In an alternative embodiment, the assay device is aligned properly by the reader with at least one device capable of moving the assay device relative to the reader. In one embodiment the assay device is moved back and forth and the signal from the at least one alignment verification zone is recorded whereby the alignment verification zone is such that a maximum signal occurs in the correct position. The reader subsequently positions the assay device correctly.

Only when the label has been detected in both the first and second areas is the determination of the amount of label in the reaction zone, or a result based on an interpretation of said amount, displayed to the user. This method guarantees that no result is displayed to the user unless there is evidence that the assay has been correctly performed. Importantly, in the case of errors or deviations, the user is immediately informed and prompted to repeat the assay. This saves valuable time, in particular in an emergency room setting.

The inventors also make available a method of verifying the operation of both the assay device or test strip, and the reader, including a calibration step. It is an advantage that the verification can be carried out using a reader with one detector. In addition to the method steps described above, a determination of the amount of label, pre-dispensed in a third area of the assay device, separate from the fluid passage, is performed. The amount of label is known, and is in one embodiment used for calibrating the reader. In case the reader detects a signal within a pre-determined margin of error, it is assumed that the reader is operational and it is calibrated so that the result reflects the true amount of label. If the reader detects a signal outside said margin of error, it is assumed that the reader is non-operational and needs maintenance.

The reader is in one embodiment programmed to either display the result or the error margin, based on the calibration results, or to alert the user if the margin of error is too high relative the absolute result. The reader can also be programmed to alert the user that maintenance or further calibration is needed, that certain components need to be replaced or that the device is non-functional.

Another embodiment of the invention is a method of performing an assay on a liquid sample using a detection conjugate capable of binding to an antigen and containing a label, using a device having at least one fluid passage, a sample addition zone and an absorbing zone, wherein the progression of the mixture of the sample and detection conjugate is measured in said fluid passage, and the recorded kinetics of the conjugate transport used to improve the accuracy of the determination of said label in said reaction zone.

According to this embodiment, the amount of detection conjugate or label, which has passed the reaction zone is determined, and the information used to determine the accuracy of the assay. In an alternative embodiment the device is programmed not to display the result until at least 50%, preferably more than 60%, more preferably at least 70%, preferably at least 80%, most preferably at least 90% or most preferably at least 95% of the detection conjugate has passed the reaction zone. Alternatively, the reading of the result is correlated to a point in time when a pre-determined amount of label has reached or passed the reaction zone.

This embodiment is focused on determining the kinetics of the reaction, and the information obtained can be used in various ways to improve the accuracy and reliability of the assay. A person skilled in the art will be able to set up a sequence of determinations and adapt available software or develop new software to handle this information.

From the description it is clear that there are a number of advantages for the present invention. Advantages include the possibility of using one detector in a reader to perform several functionality checks, calibration, and verification of the alignment for the assay device including the reading of the result itself The embodiments of the invention address many of the disadvantages associated with known devices, and may involve further advantages, apparent to a skilled person upon study of the present description and claims.

Although the invention has been described with regard to its preferred embodiments, which constitute the best mode presently known to the inventors, it should be understood that various changes and modifications as would be obvious to one having the ordinary skill in this art may be made without departing from the scope of the invention as set forth in the claims appended hereto.

The invention claimed is:

1. A method of conducting an assay, comprising:
   verifying the alignment of an assay device in a reader using at least one alignment verification zone disposed on the assay device;
   adding a sample and detecting at least one reaction between the sample and one or more reagents using the assay device, the assay device having at least one fluid passage, a sample addition zone, a reaction zone and an absorbing zone, said one or more reagents including a detection conjugate capable of binding to an antigen and containing a label;
   determining the presence of the label in a first area downstream from the sample addition zone in which the absence of signal or detection of an insufficient signal is taken as an indication of error;
   said method further comprising a calibration step, wherein the amount of at least one label, pre-dispensed in a zone for calibration on the assay device, separate from the fluid passage, is determined and the amount compared to a preset value.

2. The method according to claim 1, the reader including a display, the method further comprising:
   displaying an error message without delay, including prompting a user to remove the assay device from the reader and attempt a new assay.

3. The method according to claim 1, wherein the result of the analysis is adjusted based on the result of the calibration step.

4. The method according to claim 3, the reader including a display, the method further comprising:
   displaying a margin of error, based on the result of said calibration step to a user together with the result of the analysis.

5. The method according to claim 1, wherein said predispensed label is the same label used in said detection conjugate.

6. The method according to claim 1, further comprising:
   using the reader, determining the amount of detection conjugate which has passed the reaction zone based on the amount of label detected.

7. The method according to claim 1, wherein the kinetics of the reaction are determined based on the amount of detection conjugate determined over a range of time.

8. The method according to claim 1, further comprising:
   measuring the progression of the mixture of the sample and detection conjugate and recording the kinetics of the conjugate transport.

* * * * *